United States Patent [19]
Vedejs et al.

[11] Patent Number: 5,646,287
[45] Date of Patent: Jul. 8, 1997

[54] REAGENTS FOR ENANTIOSELECTIVE ACYLATION AND RELATED REACTIONS

[75] Inventors: Edwin Vedejs; Xinhai Chen, both of Madison, Wis.

[73] Assignee: Wisconsin Alumni Research Foundation, Madison, Wis.

[21] Appl. No.: 442,580

[22] Filed: May 17, 1995

[51] Int. Cl.$^6$ .................................. C07D 213/30
[52] U.S. Cl. .................... 546/312; 544/124; 544/360; 546/193; 546/276.4
[58] Field of Search ..................... 544/124, 360; 546/193, 281, 312

[56] References Cited

PUBLICATIONS

Chinchilla, R. et al, Tetrahedron: Asymmetry, 1990, 1(12), pp. 851–854.
Knowles, Acc. Chem. Res., 16 (1983) p. 106.
Halpern, Science, 217 (1982) p. 401.
Chen et al., Angew. Chem. Int. Ed. Engl., 28 (1989) pp. 695–707.
Klibanov, Acc. Chem. Res., 23 (1990) pp. 114–120.
Evans et al., Tetrahedron Lett., 34 (1993) pp. 5563–5566.
Kessar et al., J. Chem. Soc. Chem. Commun., (1991) p. 570.
Bolm et al., Chem. Ber., 125 (1992) p. 1169.
Whitesides et al., Angew. Chem. Int. Ed. Engl., 24 (1985) pp. 617–638.
Weidmann et al., Bulletin de la Société Chimique de France, (1967) No. 1, pp. 117–124.

*Primary Examiner*—C. Warren Ivy
*Assistant Examiner*—Garth M. Dahlen
*Attorney, Agent, or Firm*—Teresa J. Welch; Stroud, Stroud, Willink, Thompson & Howard

[57] ABSTRACT

The invention provides a method for synthesizing chiral compounds utilizing novel catalysts which are enantioselective electrophiles via kinetic resolution. The method includes treating a racemic mixture with a reagent which is a chiral DMAP derivative, a chloroformate, a trialkylamine and a Lewis acid to preferentially form a product of one of the enantiomer pair of the mixture. The invention also provides a method for resolving racemic mixture via parallel kinetic resolution.

22 Claims, 2 Drawing Sheets

REAGENTS FOR ENANTIOSELECTIVE ACYLATION AND RELATED REACTIONS

This invention was made with Government support under NSF Grant No. CHE-9207513 awarded by the National Science Foundation. The U.S. Government has certain rights in this invention.

TECHNICAL FIELD

This invention relates generally to chiral syntheses, i.e., enantioselective reactions, and in particular, to enantioselective acylation and related reactions and reagents for those reactions. The invention is particularly well-suited for enantioselective acylation of secondary alcohols.

BACKGROUND OF THE INVENTION

That asymmetry is as much a part of nature as is symmetry has long fascinated both scientists and nonscientists. Even today the fact that asymmetric molecules are usually the products of living processes remains as much a mystery as ever. Interest in synthesizing many of the products (and their intermediates) of living processes has, of course, spawned entire areas of research in chemistry and biochemistry. Considerable effort has focused on synthetic routes for chiral compounds, i.e., enantioselective or enantiospecific syntheses where only one of the chiral pair is the product of the synthetic process.

This area has found broad application, particularly in the pharmaceutical industry which is based in part on the desire for efficient syntheses and in part on regulatory constraints. Recently, regulatory pressures increasingly favor the production of enantiomerically pure substance, rather than racemates. It has been found, in some cases, that the inactive enantiomer may not be simply inert but, in fact, harmful.

Chiral syntheses span a broad range of approaches. Many rely on kinetic resolution, i.e., the fact that one enantiomer of the chiral pair to be resolved will react at a faster rate with a chiral reagent or in the presence of an optically active catalyst than the other. Chiral synthesis using optically active transition-metal catalysts has been an area of research activity. See, e.g., Knowles, *Acc. Chem. Res.* 16 (1983) p. 106; Halpern, *Science* 217 (1983) p. 401.

Probably the best known methods relying on kinetic resolution use biological catalysts, i.e., enzymes. For example, the use of esterases and lipases for kinetic resolution such as the hydrolysis of meso-diesters has proven an attractive strategy for obtaining chiral synthons. See, e.g., Chen et al., *Angew. Chem. Int. Ed. Engl.* 28 (1989) pp. 695–707; Klibanov, *Acc. Chem. Res.* 23 (1990) pp. 114–120. Lipases are attractive because they recognize a large variety of substrates. Their natural role, however, in triglyceride formation and cleavage does not place a premium on enantioselectivity and both enantiomers of a chiral substance are often recognized at the active site. Moreover, lipase esterifications can be reversible, and undesired equilibria can be a problem. Also, enantioselectivity tends to be best in organic solvents where the degree as well as the sense of selection can depend on the solvent and also on the source of the lipase, and the reactions are usually heterogeneous. Enantioselectivities ranging from barely acceptable (E<10, wherein E is enzymatic enantioselectivity) to spectacular (E>100) are reported, but, as noted above, optimization of conditions as well as choice of lipase can be crucial.

More recently, chemical acylation methods utilizing kinetic resolution have begun to emerge as another strategy for chiral synthesis. See, e.g., Evans et al., *Tetrahedron Lett.* 34 (1993) pp.5563–5566. While at the present time, there is no contest between lipase techniques and existing chemical methods for acylation and ester hydrolysis, chemical methods offer some attractive features. The reactions are generally irreversible and no undesired equilibria are present. Chemical catalysts can be made in both enantiomeric forms. Chemical catalysts can be used tinder homogeneous conditions. Ideally, they would constitute a tiny fraction of the material to be processed, and can be readily recovered.

The chemical enantioselectivity s is the counterpart to enzymatic enantioselectivity E. Kagan's equation for s for the kinetic resolution (KR) of a given substrate (e.g., a secondary alcohol) reacting by pseudo-first order kinetics is given by:

$$\text{product: } s = \frac{\ln[1 - C(1 + ee')]}{\ln[1 - C(1 - ee')]}$$

$$\text{recovered starting material: } s = \frac{\ln[(1 - C)(1 + ee)]}{\ln[(1 - C)(1 - ee)]}$$

where C is the conversion (in mol %; sum of both reacting enantiomers) while ee and ee' are the enantiomeric excess values of unreacted alcohol and the product, respectively. The enantiomer excess ee is similar to optical purity; ee is the proportion of (major enantiomer)—(minor enantiomer). For example, a 90% optical purity is 90% ee, i.e., the enantiomer ratio is 95:5, major:minor. Using as an example acylation of a secondary alcohol via kinetic resolution, if s=50, the ee' value of the chiral ester product of kinetic resolution remains above 90% until the conversion exceeds 46%. For example, the unreacted (chiral) alcohol reaches 89% ee at 50% conversion (C=0.5) and 99% ee at 55% conversion. Theoretically, the less reactive alcohol enantiomer could therefore be recovered with 90% efficiency and 99% ee (45% yield based on racemic alcohol). Impressive selectivities s in the range of 20–30 have been reported; see, Evans et al., *Tetrahedron Lett.* 34 (1993) pp.5563–5566.

While kinetic resolution (KR) techniques have provided impressive selectivities, KR suffers from some disadvantages. Over the course of the KR reaction, a large change in enantiomer ratio occurs which works increasingly against high enantioselectivity in the products. A high selectivity is needed to compensate for this effect. If values of s=200 could be achieved, highly efficient recovery of both the product of the more reactive enantiomer and the less reactive enantiomer is possible. Such selectivity is rare, even for lipases.

Despite recognition and study of various aspects of chemical methods of kinetic resolution of enantiomers, there remains a need for practical techniques for use of optically active nonenzymatic compounds for chiral syntheses.

SUMMARY OF THE INVENTION

The present invention provides a method for synthesizing chiral compounds utilizing novel catalysts which are enantioselective electrophiles capable of resolving or desymmetrizing electron-rich substrates, such as alcohols, amines and alkenes. While the method generally depends upon kinetic resolution, the invention also provides an improved kinetic resolution in a method of parallel kinetic resolution of enantiomers.

The foregoing, and other advantages of the present invention, are realized in one aspect thereof in a method for resolving a racemic mixture of a pair of enantiomers via kinetic resolution. The method includes the steps of treating the racemic mixture with a reagent comprising a chiral DMAP derivative, a chloroformate, a trialkylamine and a Lewis acid to form a product of one of the enantiomers and separating the product. The racemic mixture is suitably a secondary alcohol, a secondary amine or an alkene. In an illustrated embodiment, the racemic mixture is a secondary alcohol which has the formula $R^1CH(CH_3)OH$ wherein $R^1$ is an aryl or alkenyl group. The chiral DMAP derivative has a general formula (II), described hereinafter. The cloroformate has a general formula (I), described hereinafter.

In another aspect, the invention provides a composition which is capable of resolving a racemic mixture. The composition in admixture includes a chiral DMAP derivative, a chloroformate, a trialkylamine and a Lewis acid. The chiral DMAP derivative is represented by the general formula (II):

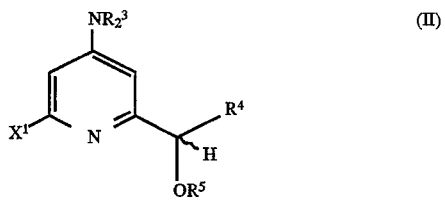

(II)

wherein $R^2$ is a $C_1$ to $C_7$ alkyl group or $NR^3_2$ is a cyclic amine group which is pyrrolidinyl, piperidinyl, piperazinyl or morpholinyl; $X^1$ is hydrogen, halogen, alkyl, aryl or heteroaryl; $R^4$ is a $C_1$ to $C_7$ branched or unbranched alkyl group; and $R^5$ is hydrogen, alkyl, benzyl, aryl, heteroaryl or acyl. The chiral DMAP derivative constitutes another aspect of the invention.

In a further aspect, the invention entails a method of resolving a racemic mixture of a pair of enantiomers via parallel kinetic resolution. The method includes the steps of treating the mixture with a reagent which includes a first DMAP derivative formed from a first chiral DMAP compound and a first chloroformate, a second DMAP derivative formed from a second chiral DMAP compound of opposite chirality and a second chloroformate, a trialkylamine and a Lewis acid to form a different predominant product for each of the enantiomer pair and separating the products.

In yet another aspect, the invention provides a composition comprising in admixture, which is capable of resolving a racemic mixture, a first DMAP derivative formed of a first chiral DMAP compound and a first chloroformate, a second DMAP derivative formed of a second DMAP derivative of opposite chirality and a second chloroformate, a trialkylamine and a Lewis acid.

In still another aspect, the invention entails a method of resolving a racemic mixture of a pair of enantiomers, which method comprises the steps of treating the mixture with a reagent comprising a first chiral reagent reactive with one of the pair, a second chiral reagent of opposite chirality reactive with the other one of the pair, in a single phase solvent sufficient to support reaction of the first reagent with one of the pair of enantiomer and the second reagent with the other of the pair of enantiomers to form a different predominant product for each of the enantiomer pair and separating the products.

In yet another aspect, the invention is a composition comprising in admixture, which is capable of resolving a racemic mixture of a pair of enantiomers, a first chiral reagent preferentially reactive to one of the pair of enantiomers, a second chiral reagent of opposite chirality to the first reagent preferentially reactive with the other one of the pair, in a single phase solvent sufficient to support reaction of the first reagent with one of the pair of enantiomer and the second reagent with the other of the pair of enantiomers.

Other advantages and a fuller appreciation of the specific attributes of this invention will be gained upon an examination of the following detailed description of preferred embodiments and appended claims taken in conjunction with the figures of the drawing. It is expressly understood that the drawing is for the purpose of illustration and description only, and is not intended as a definition of the limits of the invention.

BRIEF DESCRIPTION OF THE DRAWINGS

The preferred exemplary embodiment of the present invention will hereinafter be described in conjunction with the appended drawing wherein like designations refer to like elements throughout and in which.

DETAILED DESCRIPTION

Figure 1:
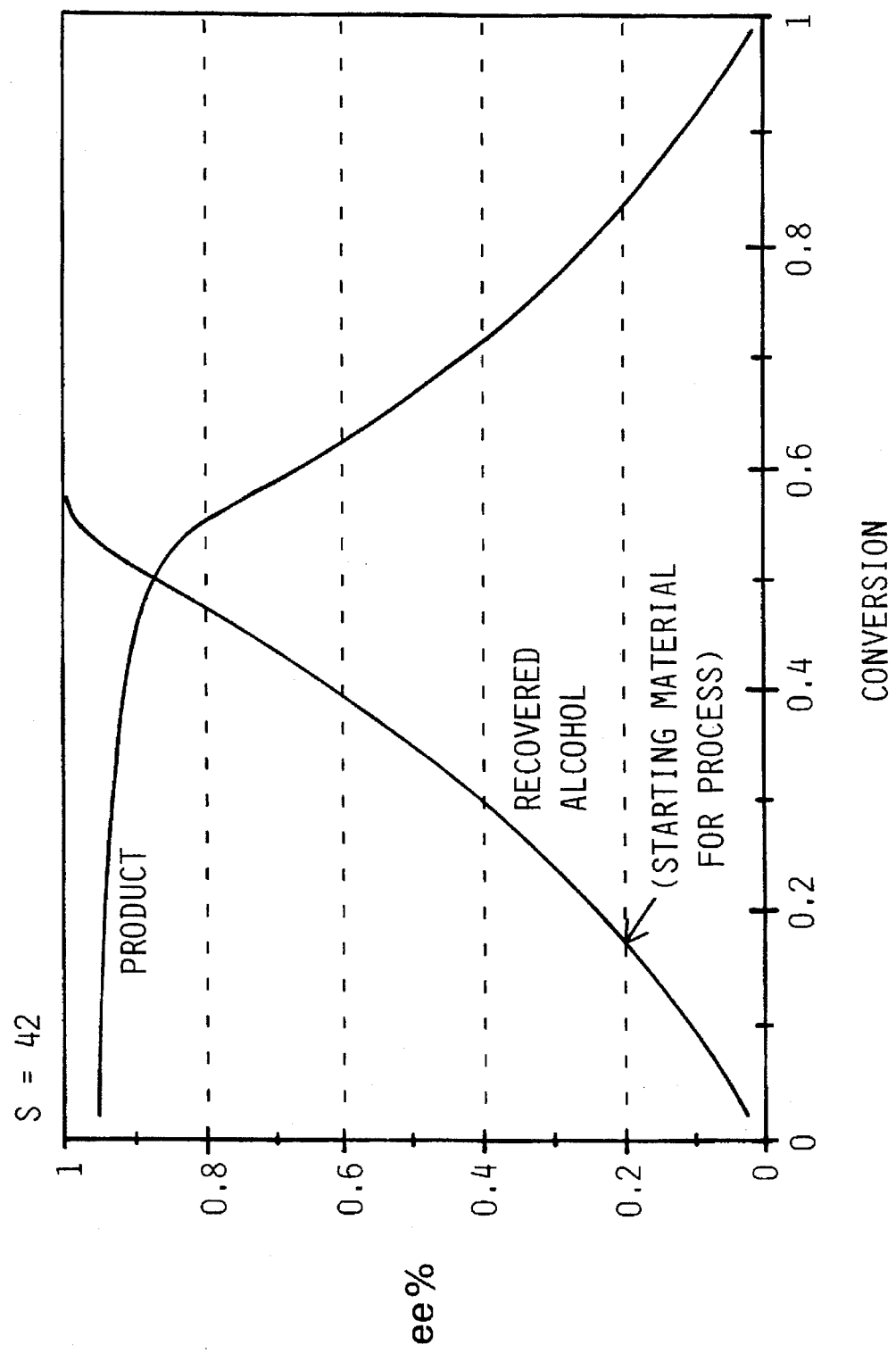
FIG. 1 is a graph depicting the change in % ee for enantiomer product with the increase % conversion of the starting racemic material for s=42.

The present invention relates broadly to chiral syntheses. However, the method of the present invention is most particularly adapted for use in generating enantioselective electrophiles capable of resolving or desymmetrizing electron-rich substrates, such as alcohols, amines and alkenes. Accordingly, the present invention will now be described in detail with respect to such endeavors; however, those skilled in the art will appreciate that such a description of the invention is meant to be exemplary only and should not be viewed as limitative on the full scope thereof.

The present invention provides enantioselective electrophilic agents and methods of preparing and using such agents. The present invention is characterized by an ability to provide enantioselective reactions that are homogeneous and are irreversible, and the agent can be readily removed from the reactions system. The yield of the enantiomerically enriched substances can be improved with a technique of parallel kinetic resolution (PKR). These attributes are achieved through a novel combination of physical and chemical features and reaction conditions.

In the following description of the method of the invention, process steps are carried out at room temperature and atmospheric pressure unless otherwise specified. As used herein, the terms "compound(s)" and "derivative(s)" are meant to be construed broadly as referring to both pure compounds and substituted compounds and when used in the same sentence or claim is meant to indicate two different compounds of different structure; i.e., differently substituted. The terms "preferential" and "preferentially" in relation to reaction rates are meant to refer to the fact that enantiomers of a chiral pair react at different rates with a reagent with one reaction rate being substantially faster than the other. The term "predominant" in relation to a product of a reaction of enantiomers with a reagent is meant to refer to the product formed in the larger amount due to the differences in the rates of reaction.

In one of its aspects, the invention is a method of resolving or desymmetrizing nucleophiles, such as alcohols or amines using carbonyl, phosphoryl, silyl or sulfonyl electrophiles. That is, the invention is a synthetic route for enantioselective acylation, phosphorylation, silylation and sulfonylation reactions utilizing novel reagents. In an illustrated embodiment, the invention is a method of kinetic resolution of optically active secondary alcohols of the general formula, R*OH where R* represents a chiral center and where R is generally a unsubstituted or a substituted alkyl or aryl group. Preferred are those secondary alcohol of the general formula R¹CH(CH₃)OH wherein R¹ is an aryl, heteroaryl or alkenyl group. As used herein and in the art, "heteroaryl" refers to heterocyclic compounds containing nitrogen (e.g., pyridine) or oxygen (e.g., furan) or rings containing both nitrogen and oxygen.

The method of the present invention includes treating a racemic mixture of a chiral compound, e.g., a secondary alcohol, with a reagent, in a concentration sufficient to effect resolution, which reagent comprises, in admixture, a Lewis acid, a tertiary amine, a chloroformate and a chiral derivative of 4-dimethylaminopyridine, the latter acting as a catalyst for the reaction.

A Lewis acid, $MX_n$, in accordance with the present invention includes compounds wherein M is a cation of the elements of groups IIA, IIB and VIII, X is an anion of the elements of group VIIA, and n has a value which is 2 or 3. Preferably, M is a cation which is $Zn^{2+}$, $Mg^{2+}$, $Ca^{2+}$, $Ni^{2+}$ or $Fe^{3+}$ and X is a anion which is $Cl^-$, $Br^-$, $OSO_2CF^{-1}_3$, $NO^{-1}_3$ or $BF^-_4$. Most preferred are those Lewis acids where M is $Zn^{2+}$ or $Mg^{2+}$ and X is a simple halide, namely, $Cl^-$ and $Br^-$ For example, preferred Lewis acid compounds include $ZnCl_2$ and $MgBr_2$. The most preferred and advantageous form of the Lewis acid in accordance with the present invention is anhydrous.

The chloroformate in accordance with the present invention is of the general formula (I): Cl—C(O)—OR² wherein R² is a functional group which is menthyl, cyclohexyl, ethyl, 1-adamantyl, 9-fluorenyhnethyl, trichloroethyl, phenyl or vinyl. Preferred is the compound 2,2,2-trichloro-1,1-dimethylethyl chloroformate, $Cl_3C$—$C(CH_3)_2$—$O$—$C(O)$—Cl.

A chiral 4-dimethylaminopyridine (DMAP) derivative in accordance with the present invention is represented by the general formula (II):

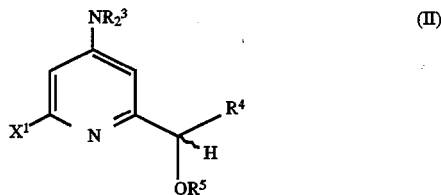

wherein R³ is a C₁ to C6 alkyl group or NR³₂, is a cyclic amine such as pyrrolidinyl, piperidinyl, piperazinyl or morpholinyl; X¹ is hydrogen, halogen, alkyl, α-alkoxylalkyl, aryl or heteroaryl; R⁴ is a C₁ to C₆ branched or unbranched alkyl group; and R⁵ is hydrogen, alkyl, benzyl, aryl, heteroaryl or acyl. Examples of suitable aryl groups include phenyl, tolyl, naphthyl, and 5,6-benzo. Examples of suitable heteroaryl groups include picoline, pyridine, furan, pyrrolidine, thiophene, triazole, oxazole, oxazoline, imidazole, imidazoline, tetrazole, and oxadiazole. In a preferred embodiment, the compound of formula (II) is that in which R³ is methyl, R⁴ is t-butyl and X¹ is hydrogen. Most preferred are those compounds of formula (II) wherein R⁵ is hydrogen. In the formulas in the specification and in the claims, a wavy line to a substituent, e.g., to H₅, indicates that the substituent can exist in stereoisomeric alternate forms.

Compounds of formula (I) are commercially available. For example, the preferred chloroformate, $Cl_3C$—$C(CH_3)_2$—O-C(O)—Cl, is available from Aldrich Chemical Co. Compounds of formula (II) can be synthesized from methods described in the art, for example, Singh et al., *J. Chem. Soc. Chem. Commun.* (1991) p. 570; Bohn et al., *Chem. Ber.* 125 (1992) p. 1169. For example, DMAP is converted into the BF₃ adduct, metalated in the 2-position using lithium tetramethylpiperidide, and acylated with pivaloyl chloride to give a ketone with a general structure such as that shown in Reaction Scheme 1 below and referred to as numeral 1.

Reaction Scheme 1 shows an illustrated embodiment for production of 2-(1-methoxy-2',2'-dimethylpropyl)-4-dimethylaminopyridine, a compound of formula (II) and referred to as numeral 3, i.e., the reaction scheme generally depicts the conversion of ketone I to methoxy derivative 3.

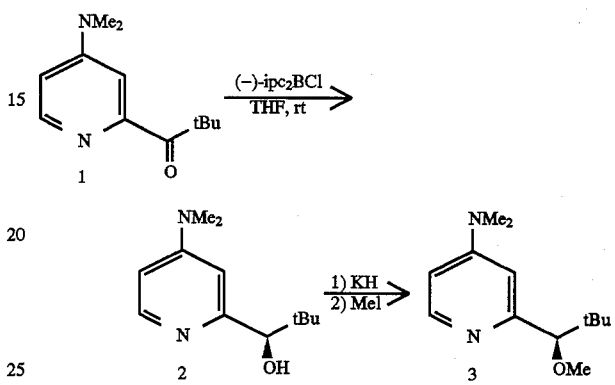

Reaction Scheme 1

Specifically, for the exemplary reaction given in Reaction Scheme 1, 2-trimethylacetyl-4-dimethylaminopyridine (ketone 1) is reduced with (−)-B-chlorodiisopinocampheylborane (ipc₂BCl) to produce 1-[2'-(4-dimethylaminopyridine)]-2,2-dimethylpropanol (alcohol 2) which is methylated with methyl iodide/potassium hydride, (CH₃I/KH) to form methoxy derivative 3.

Reaction Scheme 2, given below, depicts a typical enantioselective reaction in accordance with the present invention. In the specific example of Reaction Scheme 2, the product of Reaction Scheme 1, i.e., the methoxy derivative 3 as the DMAP derivative of formula (II), 2-(1-methoxy-2', 2'-dimethylpropyl)-4-dimethylaminopyridine, is used as the starting material and catalyst.

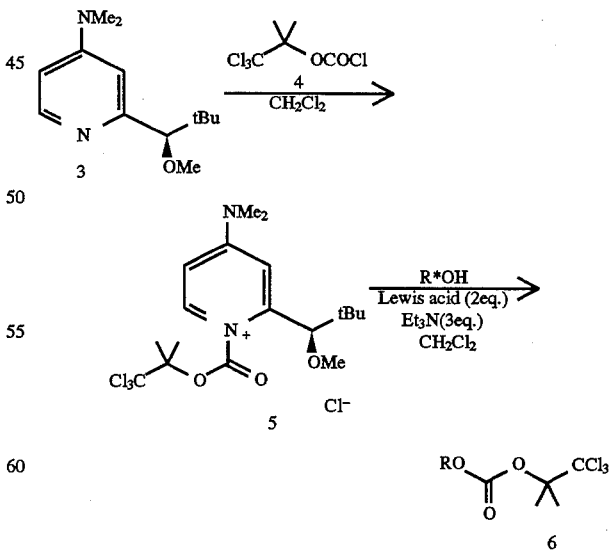

Reaction Scheme 2

Specifically, methoxy derivative 3 is treated with 2,2,2-trichloro-1,1-dimethylethylchloroformate (chloroformate 4) to produce the corresponding pyridinium salt 5 to which is added triethylamine and a Lewis acid in accordance with the present invention. The resulting admixture is reacted with a secondary alcohol R*OH to produce the product 6. The enantiomer selectivity s was found to be between about 26–42 for the range of R*OH compounds tested. Selectivity factors of this magnitude are comparable to the enzymatic methods. The method of the present invention, however, has the advantage that it is a homogeneous catalytic reaction; the reaction is irreversible and the chiral DMAP derivative 3 is readily removed from the reaction product mix by extraction with dilute acid followed by neutralization.

Parallel Kinetic Resolution (PKR)

While kinetic resolution provides an effective method for resolving a mixture of enantiomers, as explained hereinbefore, it is not without its disadvantages. The method, of course, depends on the rate of reaction of one enantiomer being different from the other for a particular reagent. However, as the amount of more reactive enantiomer decreases, i.e., is converted, its concentration decreases and a point is reached where the probability that the less reactive enantiomer will react becomes high and the "slow" reaction becomes the dominant reaction. For example, take a chiral racemic alcohol, d,l - R*OH that reacts with a chiral enantiomerically pure activated ester d - Z*C(O)OMe, wherein Z* is the chiral leaving group, with an excellent selectivity factor s=33. According to Kagan's equation, at 50% conversion the product R*OC(O)OMe as well as the recovered R*OH would have marginally acceptable 85% ee. Further conversion would erode the product ee and enhance the starting material ee at the cost of decreased recovery. Of course, at 100% conversion, the product must be racemic.

Figure 2:
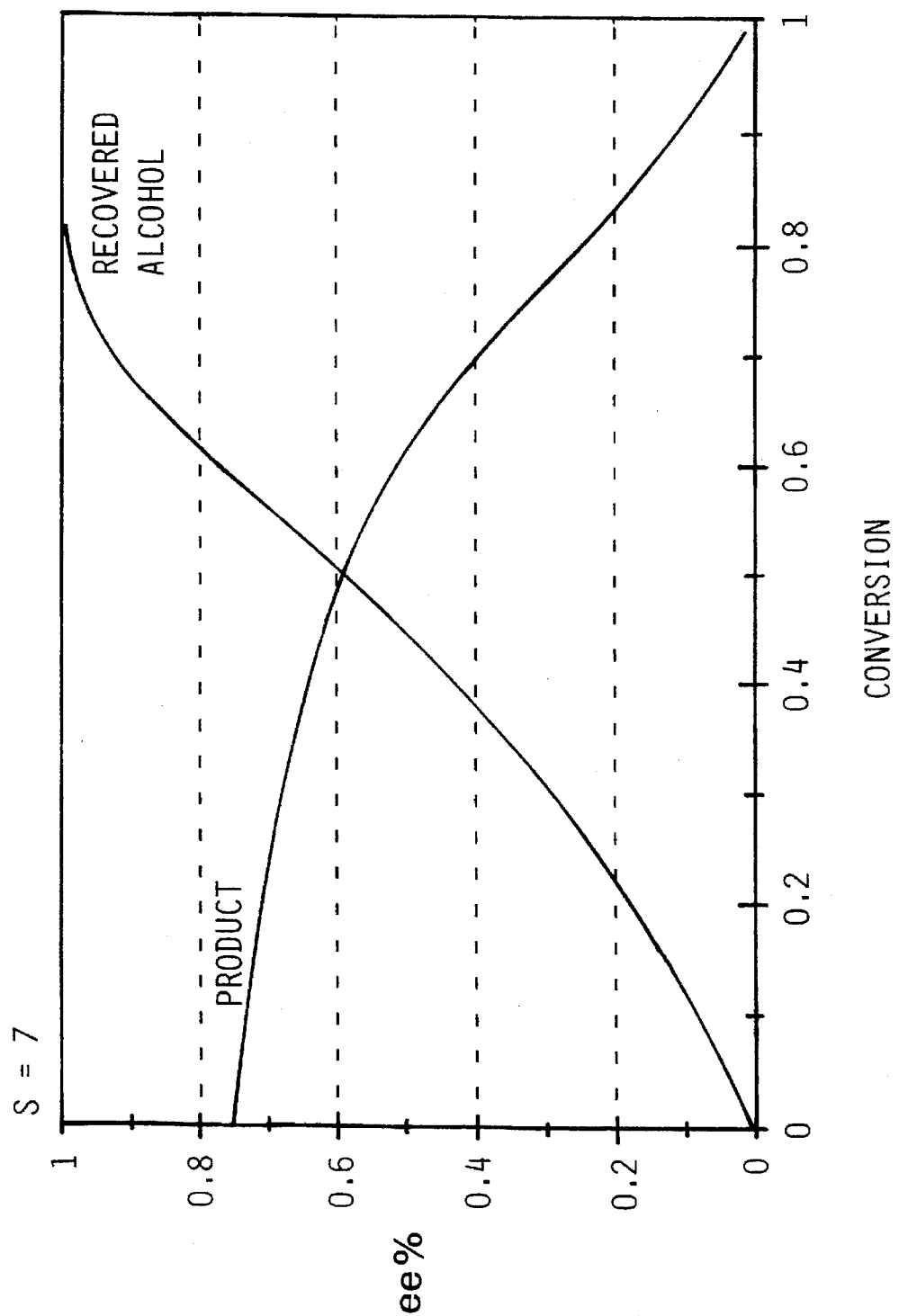
FIG. 2 is a graph of the same parameters as FIG. 1 for s=7.

This situation is further illustrated in FIGS. 1 and 2. If one begins with a racemic mixture, i.e., a 50:50 mix of enantiomers. At the start of a reaction, ee=0. If, for example, s=42 (an excellent selectivity factor for chemical acylation), at initial conversion the ee is about 95%. As the % conversion continues, there is a point at about 55 % conversion that the ee begins to drop precipitously, as shown in FIG. 1. The situation is even more dramatic where s is small, e.g., s=7. In this case, even initially, the ee never reaches even 80% ee and begins decreasing substantially simultaneously with the initial conversion.

Parallel kinetic resolution (PKR) provides a somewhat different approach, one which avoids the problem of the "slow", i.e., less reactive, enantiomer reaction becoming statistically more competitive. If, for example, a chiral racemic alcohol is reacted with equal amounts of activated esters having different alkoxycarbonyl groups connected to opposite enantiomers of the chiral leaving group, e.g., d-Z*C(O)OMe and/-Z*C(O)OBn where OMe is methoxy and OBn is benzyloxy, and the activated esters have substantially the same intrinsic reactivities and the same selectivities, e.g., s=33, the benzyloxycarbonalyation of one enantiomer of R*OH will occur at approximately the same rate as the methoxycarbonaylation of the other enantiomer, and the ratio of d-R*OH to l-R*OH will not change throughout the reaction. Theoretical calculations have shown that in the ideal case, the different products R*OC(O)OMe and R*OC(O)OBn from each enantiomer of R*OH can be produced with identical 94% ee values at 100% conversion. The ideal situation competes in enantioselectivity and efficiency with the rare "ideal" lipase (E=200; 96% for both the product and the recovered alcohol at 50% conversion). However, even a moderate selectivity factor of s=20 would give both products with 90% ee at 100% conversion using PKR, if the rates of acylation are equal.

An illustrated synthetic route utilizing the PKR principle is given below as Reaction Scheme 3:

Reaction Scheme 3

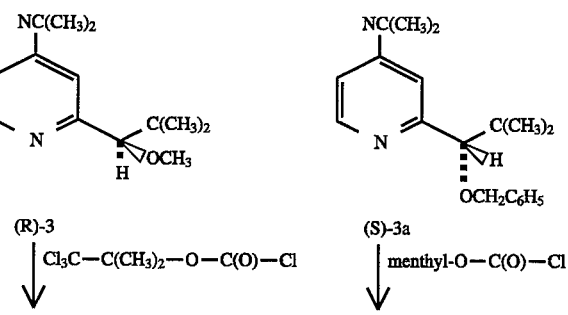

-continued
Reaction Scheme 3

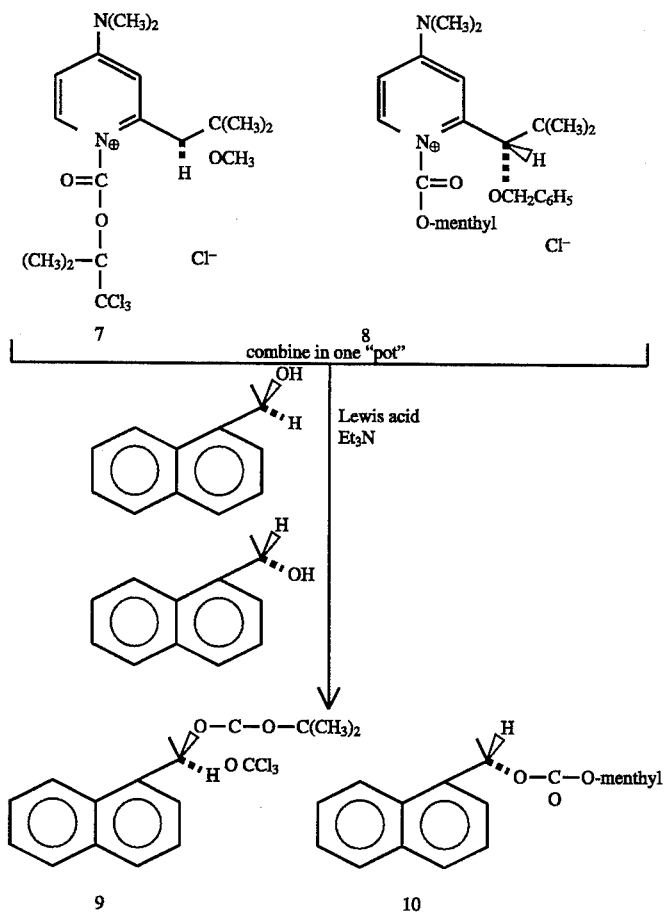

In this illustrated reaction, (R) and (S) derivatives 3 and 3a, respectively, (i.e., analogous to product 3 shown in Reaction Scheme 2) are prepared separately and the pyridinium salt form 7 and 8 are formed by reacting each with different chloroformates, 2,2,2,-trichloro-1,1-dimethylethyl chloroformate and menthyl chloroformate, respectively. The pyridinium salts 7 and 8 are then combined with the Lewis acid and triethylamine, and the racemic alcohol R*OH is then added. Because each activated ester reacts preferentially with one of the enantiomer pairs and at a similar selectivity factor, the problems of classical kinetic resolution are avoided. It was found that there was 82% ee at a 78% conversion for the product 9 and 70% de (where de is the proportion of major diastereomer minus the minor diastereomer in %) for the product 10. Diastereomers exist because of the menthyl group is chiral. This makes it easier to assay selectivity for product 10, but the method of the present invention does not require a chiral group in the ClCO$_2$R$^2$. Without PKR, the theoretical curve shown in FIG. 1 predicts <27% ee at 78% conversion for product 9.

It is understood that for certain applications the chloroformate-type reagent may advantageously take the form of a more general chloro compound of the formula Cl—Y wherein Y is a functional group which is

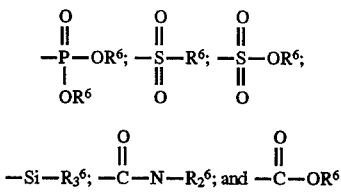

wherein R$^6$ is hydrogen, alkyl, benzyl, aryl, heteroaryl or acyl. The latter functional group, of course, is the chloroformate of formula (II).

It is expected that PKR can be used for any kinetic resolution, biological or chemical or a combination of biological and chemical. In regard to the use of PKR in biological resolution, two different enzymes are used. In the mixed biological/chemical system, an enzyme and a chemical catalyst, e.g., the DMAP derivative, are used. PKR can be used where two catalytic or stoichiometric processes work simultaneously and where each process makes a distinct product of its favored enantiomer and where these products are separable. PKR will occur with higher efficiency if the two processes do not conflict chemically or biologically.

The present invention is further explained by the following examples which should not be construed by way of limiting the scope of the present invention. Proton nuclear magnetic resonance ($^1$H-NMR) spectra were recorded with a Bruker 300 MHz or 250 MHz spectrometer in CDCl$_3$ with CHCl₃ as an internal standard. Chemical shifts are reported in ppm. Infrared (IR) spectra were recorded with a Nicolet 740 using conditions as specified in each example. Mass spectra were record with a Kratus MS-80RFA instrument. Thin layer chromatography (TLC) was performed on silica gel with the solvents indicated in each example.

Example 1: Preparation of Chiral DMAP Derivative—2-(1-methoxy-2', 2'-dimethylpropyl)-4-dimethylaminopyridine 2-Trimethylacetyl-4-dimethylaminopyridine (1)

To a solution of 4-dimethylaminopyridine (DMAP) (6.892 g, 56.4 mmol) in dry THF (200 mL) at 0° C. was added BF₃ etherate (7.3 mL, 59.4 mmol) dropwise via a syringe. A slightly cloudy colorless solution was obtained. It was stirred at 0° C. for 0.5 hr. To a solution of 2,2,6,6-tetramethyl piperidine (10.0 mL, 59.2 mmol) in dry THF (100 mL) at −78° C. in a second flask was added n-butyllithium (58.5 mL, 1.06 M in hexane, 62.0 mmol) via syringe. It was then warmed to room temperature in about 20 min. The DMAP-BF₃ salt solution was cooled to −78° C. upon which a white suspension was formed. To this suspension was added lithium tetramethylpiperidide solution (prepared in the second flask) via cannula in 0.5 hr with vigorous stirring. A clear dark tan solution was observed after the addition was complete and it was stirred for 30 min at −78° C. This solution at −78° C. was then transferred dropwise to a solution of trimethylacetyl chloride (13.9 mL, 112.6 mmol) in dry THF (50 mL) at −78° C. via cannula in 1 hr. The reaction turned orange during the addition. It was allowed to warm slowly to room temperature in 5 hr. The final solution was brown. Water (50 mL), methanol (50 mL) and 6 N HCl (30 mL) were added sequentially to the reaction mixture. The solution was stirred at 35°–40° C. overnight. The volatile solvents were removed by aspirator. The residue was made basic with 6 N NaOH (ca. pH>11) and extracted with diethyl ether (3×150 mL) and THF (150 mL). Combined organic solution was dried with MgSO₄. After removal of solvent (aspirator), the residue was purified by flash chromatography on silica gel (20×5 cm), 1:3 EtOAc/hexane eluent to give 7.10 g of 2-Trimethylacetyl-4-dimethylaminopyridine (1) (61%). Characterization of the product (1) was as follows:

Analytical TLC on silica gel. 25:1 THF/NH₄OH, $R_f$=0.70; molecular ion calc'd for $C_{12}H_{18}N_2O$: 206.14195; found m/e=206.1426, error=3 ppm; base peak=122 amu; IR (CDCL₃ cm⁻¹ 1680, C=O; 1599, C=N; 2988, C–H; 300 MHz NMR (CDCl₃, ppm) δ 8.23 (1 H, d, J=5.8 Hz) 7.08 (1 H, d, J=2.7) 6.55 (1 H, dd, J=5.8, 2.7 Hz) 3.03 (6 H, s) 1.44 (9 H, s).

1-[2'-(4'-Dimethylaminopyridine)]-2,2-dimethylpropanol (2)

To a solution of (−)-B-chlorodiisopinocampheylborane (8.80 g, 27.5 mmol, Aldrich, transferred in a dry box) in dry THF (20 mL) at room temperature was added a solution of (1) (3.82 g, 18.5 mmol) in dry THF (20 mL) via cannula. A yellow suspension was obtained. It was vigorously stirred for 3 days at room temperature. Diethanolamine (6 mL), methanol (15 mL, water (10 mL) and 6 N HCl (15 mL) were added and the reaction mixture was warmed up to 45° C. and stirred for 4 hr. EtOAc (50 mL) was then added. Two phases were separated. The organic solution was extracted with 2 N HCl (3×25 mL). Combined aqueous solution was made basic (pH>11) with NaOH pellets, and it was extracted with EtOAc (3×50 mL). Combined organic solution was dried with MgSO₄. After removal of solvent (aspirator), the residue was purified by flash chromatography on silica gel (20×5 cm), 50:50:1 THF/CHCl₃/NH₄OH eluent to give 2.70 g (70%) 1-[2'-(4'-Dimethylaminopyridine)]-2,2-dimethylpropanol (2), (R)-enantiomer.

Analytical TLC on silica gel, 25:1 THF/NH₄OH, $R_f$=0.68. Pure material was 30 obtained by crystallization from ether/hexane, mp 131°–132° C. Molecular ion calc'd for $C_{12}H_{20}N_2O$: 208.15759: found m/e=208.1574, error=1 ppm; base peak=151 amu; IR (KBr, cm⁻¹) 1602, C=N; 3346, O–H; 2949, C–H: 300 MHz NMR (CDCl₃, ppm) δ 8.16 (1 H, d, J=5.8 Hz) 6.42 (1 H, dd, J=5.8, 2.7 Hz) 6.35 (1 H, d, J =2.7 Hz) 4.22 (1 H, s) 4.20-4.08 (1 H, br, x) 3.01 (6 H, s) 0.94 (9 H, s).

The (S)-enantiomer was prepared in the same way using (2) and (+)-B-chlorodiisopinocampheylborane.

2-(1'-methoxy-2',2'-dimethylpropyl)-4-dimethylaminopyridine (3)

To a suspension of KH (0.580 g, 4.89 mmol, 35 wt % in mineral oil, Aldrich) in dry THF (10 mL) at 0° C. was added a solution of (2) (0.663 g, 3.16 mmol) in dry THF (5 mL) via cannula in 5 min. Vigorous gas evolution was observed. The reaction mixture was warmed to room temperature and stirred for 2 hr. Iodomethane (0.24mL, 3.86 mmol) was then added. After another 3 hr, water (10 mL) was added and so was 2 N NaOH solution (10 mL). The mixture was extracted with EtOAc (3×30 mL). Combined organic solution was dried with MgSO₄. After solvent was removed by aspirator, the residue was purified by flash column chromatography to give 0.527 g (75 %) 2-(1'-methoxy-2', 2'-dimethylpropyl)-4-dimethylaminopyridine (3).

Analytical TLC on silica gel, 90:10:0.2 CHCL₃/MeOH/NH₄OH, $R_f$=0.40. Pure material was obtained by crystallization from ethyl acetate, mp 56°–58° C.; molecular ion calc'd for $C_{13}H_{22}N_2O$: 222.17325; found m/e=222.1737, error=2 ppm; base peak=151 amu; IR (CDCl₃, cm⁻¹) 2958, C–H; 1603, C=N; 300 MHz NMR (CDCl₃, ppm) δ 8.18 (i H, d, J=6.2 Hz) 6.58 (1 H, d, J=2.7 Hz) 6.43 (1 H, dd, J=6.2, 2.7 Hz) 3.88 (1 H, s) 3.26 (3 H, s) 3.02 (6 H, s) 0.94 (9 H, s).

2-(1'-Benzyloxy-2',2'-dimethylpropyl)-4-dimethylaminopyridine (3a)

The same method described above for preparation of (3) was used to prepare (3a) except that benzyl bromide was used in place of iodomethane.

Analytical TLC on silica gel, 90:10:0.2 CHCl₃/MeOH/NH₄OH, $R_f$=0.45; Molecular ion calc'd for $C_{19}H_{26}N_2O$: 298.20456; found m/e 298.2053, error=2 ppm; base peak= 151 amu; IR (CDCl₃, cm⁻¹) 2955, C–H; 1602, C=O; 300 MHz NMR (CDCl₃, ppm) δ 8.20 (1 H, d, J=5.8 Hz) 7.34-726 (5 H, m) 6.67 (1 H, d, J=2.7 Hz) 6.43 (1 H, dd, J=5.8, 2.7 Hz) 4.48 (I J, d, J=12.1 Hz) 4.31 (1 H, d, J=12.1 Hz) 4.12 (1 H, s) 2.99 (6 H, s).

General Procedure for Kinetic Resolution

The following Examples 2–8 demonstrate the preparation of compounds of formula (II), i.e., compounds of structure similar to (6) in Reaction Scheme 2. All examples used the following general procedure except for the chiral alcohol used.

To a solution of chiral DMAP derivative 3 (0.15 mmol) in CH₂Cl₂ (1 mL) at 0° C. was added a CH₂Cl₂ solution of chloroformate 4 (0.14 mmol; Aldrich Chemical Co.). The reaction mixture was warmed to room temperature and stirred for 2 hr. A solution of Lewis acid (0.5 M $ZnCl_2$, dried by fusion with Bunsen flame under vacuum, in diethyl ether; or 0.23 M $MgBr_2$ in tetrahydrofuran (THF), prepared by Grignard reaction of 1,2-dibromoethane with excess magnesium) was then added. After 10 min, the racemic aromatic secondary alcohol (0.3 mmol) and triethylamine were added sequentially. The resulting clear solution was stirred at room temperature under a nitrogen atmosphere for the specified time given in Table I below. The products and the alcohol substrate ware isolated by running the reaction mixture through a silica gel plug (4×1.5 cm) eluted with 50:50 ethyl acetate (EtOAc)/hexane (40 mL). The percent conversion of the alcohol was determined by $^1$H-NMR integration dam. The product carbonate and the recovered alcohol were purified by flash column chromatography with 4:96 and 20:80 EtOAc/hexane as eluent, respectively. The enantiomeric excess of these materials was determined by HPLC analysis on columns with chiral stationary phases. When necessary, the product carbonate was hydrolyzed to the alcohol (1 N KOH solution in 1:2:1 $MeOH/H_2O$THF) for the HPLC analysis.

Example 2: α-methyl-1-naphthalenemethanol 2',2', 2'-trichloro-1',1'-dimethylethanol carbonate After removal of solvent (aspirator), the residue was purified by flash chromatography on silica gel (20×1.5 cm) 4:96 EtOAc/hexane eluent; analytical TLC on silica gel: 1:4 EtOAc/hexane, $R_f$=0.69; molecular ion calc'd for $C_{17}H_{17}Cl_3O_3$: 374.0244; found m/e=374.0228, error=4 ppm; base peak=155 amu; IR ($CDCl_3$, $cm^{-1}$) 2992, C–H; 1748, C=O; 300 MHz NMR ($CDCl_3$, ppm) δ8.05 (1 H, d, J=8.2 Hz) 7.90-7.70 (2 H, m) 7.63 (1 H, d, J=7.0 Hz) 7.58-7.46 (3 H, m) 6.48(1 H, q, J=6.6 Hz) 1.93 (3 H, s) 1.84 (3 H, s) 1.76 (3 H J=6.6 Hz).

Example 3: α-methyl-2-naphthalenemethanol 2',2', 2'-trichloro-1',1'-dimethylethanol carbonate After removal of solvent (aspirator), the residue was purified by flash chromatography on silica gel (20–1.5 cm) 4:96 EtOAc/hexane eluent; analytical TLC on silica gel: 1:4 EtOAc/hexane, $R_f$=0.58; molecular ion calc'd for $C_{17}H_{17}Cl_3O_3$: 374.0244; found m/e=374.0239, error=1 ppm; base peak=155 amu; IR ($CDCl_3$, $cm^{-1}$) 2986, C–H; 1746, C=O; 300 MHz NMR ($CDCl_3$, ppm) δ 7.87-7.83 (4 H, m) 7.52-7.48 (3 H, m) 5.87 (1 H, q, J=6.6 Hz) 1.94 (3 H, s) 1.84 (3 H, s) 1.69 (3 H, d, J=6.6 Hz).

Example 4: α-methylbenzylalcohol 2',2', 2'-trichloro-1',1'-dimethylethanol carbonate After removal of solvent (aspirator), the residue was purified by flash chromatography on silica gel (20–1.5 cm) 4:96 EtOAc/hexane eluent; analytical TLC on silica gel: 1:4 EtOAc/hexane, $R_f$=0.57; molecular ion calc'd for $C_{13}H_{15}Cl_3O_3$: 374.00879; found m/e=374.0073, error=5 ppm; base peak=105 amu; IR ($CDCl_3$, $cm^{-1}$) 2990, C–H; 1746, C=O; 300 MHz NMR ($CDCl_3$, ppm) δ 7.38-7.27 (5 H, m) 5.70 (1 H, q, J=6.6 Hz) 1.93 (3 H, s) 1.85 (3 H, s) 1.60 (3 H, d, J=6.6 Hz).

Example 5: 1-phenylpropanol 2',2',2'-trichloro-1',1'-dimethylethanol carbonate

After removal of solvent (aspirator), the residue was purified by flash chromatography on silica gel (20–1.5 cm) 4:96 EtOAc/hexane eluent; analytical TLC on silica gel: 1:4 EtOAc/hexane, $R_f$=0.59. Pure material was obtained by crystallization from hexane, mp 37.5°–38.5° C. No parent ion for $C_{14}H_{17}Cl_3O_3$: $C_{10}H_{11}O_3$(+–, 179.0713; error=3 ppm; base peak=107 amu; IR ($CDCl_3$, $cm^{-1}$) 2973, C–H; 1746, C=O; 300 MHz NMR ($CDCl_3$, ppm) δ 7.37-7.28 (5 H, m) 5.48-5.43 (2 H, m) 1.92 (3 H, s) 1.83 (3 H, s) 0.91 (3 H, t, J=7.4 Hz).

Example 6: α-methyl-2-chlorobenzyl alcohol 2',2', 2'-trichloro-1',1'-dimethylethanol carbonate After removal of solvent (aspirator), the residue was purified by flash chromatography on silica gel (20–1.5 cm) 4:96 EtOAc/hexane eluent; analytical TLC on silica gel: 1:4 EtOAc/hexane, $R_f$=0.68. Pure material was obtained by crystallization from hexane, mp 74.5°–75.5° C.; molecular ion calc'd for $C_{13}H_{14}Cl_4O_3$: 357.96985; found m/e= 357.9656; error=11 ppm; base peak=139 amu; IR ($CDCl_3$, $cm^{-1}$) 2990, C–H; 1751, C=O; 300 MHz NMR ($CDCl_3$, ppm) δ 7.49 (1 H, dd, J=7.8, 16 Hz) 7.37-7.20 (3 H, m) 6.07 (1 H, q, J=6.6 Hz) 1.93 (3 H, s) 1.86 (3 H, s) 1.59 (3 H, d, J=6.6 Hz).

Example 7: α-methyl-2-methylbenzyl alcohol 2',2', 2'-trichloro-1',1'dimethylethanol carbonate After removal of solvent (aspirator), the residue was purified by flash chromatography on silica gel (20–1.5 cm) 4:96 EtOAc/hexane eluent; analytical TLC on silica gel: 1:4 EtOAc/hexane, $R_f$=0.65. Pure material was obtained by crystallization from hexane, mp 86°–87° C.; no parent ion for $C_{14}H_{17}Cl_4O_3$; C4H6Cl3 158.9525; error=7 ppm; base peak=119 amu; IR ($CDCl_3$, $cm^{-1}$) 2986, C–H; 1748, C=O; 300 MHz NMR ($CDCl_3$, ppm) δ 7.44-7.41 (1 H, m) 7.23-7.13 (3 H, m) 5.90 (1 H, q, J=6.6 Hz) 2.38 (3 H, s) 1.84 (3 H, s) 1.57 (3 H, d, J=6.6 Hz).

Example 8: α-methyl-4-chlorobenzyl alcohol 2',2', 2'-trichloro-1',1'-dimethylethanol carbonate After removal of solvent (aspirator), the residue was purified by flash chromatography on silica gel (20–1.5 cm) 4:96 EtOAc/hexane eluent; analytical TLC on silica gel: 1:4 EtOAc/hexane, $R_f$=0.60. Pure material was obtained by crystallization from hexane, mp 86.5°–87° C.; molecular ion calc'd for $C_{13}H_{14}Cl_4O_3$: 357.96985; found m/e=357.9669; error=8 ppm; base peak=139 amu; IR ($CDCl_3$, $cm^{-1}$) 2988, C–H; 1747, C=O; 300 MHz NMR ($CDCl_3$, ppm) δ 7.36-7.26 (4 H, m) 5.66 (4 H, m) 5.66 (1 H, q, J=6.6 Hz) 1.93 (3 H, s) 1.58 (3 H, d, I=6.6 Hz).

The results of the yields of the reactions corresponding to Examples 2–8 are summarized in Table 1 below.

TABLE 1

| Entry # | ROH | Lewis acid | Conversion of alcohol | Reaction time | Recovered ROH ee % | Selectivity factor (s) (ROH) | Product ee % | Selectivity factor (s) (product) |
|---|---|---|---|---|---|---|---|---|
| 1. | 1-(1-naphthyl)ethanol | $ZnCl_2$ | 30% | 39 h | 38% ee | 24.1 | 91% ee | 31.1 |
| 2. |  | $MgBr_2$ | 42% | 14 h |  |  | 91% ee | 42.0 |
| 3. | 1-(2-naphthyl)ethanol | $ZnCl_2$ | 31.5% | 40 h |  |  | 90% ee | 28.5 |
| 4. |  | $MgBr_2$ | 43.9% | 16 h | 62% ee | 16.2 | 89% ee | 36.0 |
| 5. | 1-phenylethanol | $ZnCl_2$ | 24.5% | 40 h |  |  | 93.2% ee | 38.2 |
| 6. |  | $MgBr_2$ | 40.8% | 40 h |  |  | 82.3% ee | 18.2 |
| 7. | 1-phenylpropanol | $ZnCl_2$ | 20.3% | 62 h | 22.1% ee | 17.5 | 89.2% ee | 22.0 |
| 8. |  | $MgBr_2$ | 39.0% | 40 h |  |  | 75.6% ee | 11.5 |
| 9. | 1-(2-methylphenyl)ethanol | $ZnCl_2$ | 21.1% | 48 h | 19.1% ee | 7.1 | 91.5% ee | 28.7 |
| 10. |  | $MgBr_2$ | 42.0% | 40 h | 60.1% ee | 19.8 | 87.6% ee | 29.1 |
| 11. | 1-(2-chlorophenyl)ethanol | $ZnCl_2$ | 30.7% | 48 h | 41.2% ee | 41.3 | 89.5% ee | 26.6 |
| 12. |  | $MgBr_2$ | 43.6% | 40 h | 68.6% ee | 34.4 | 89.2% ee | 36.1 |

Example 9: Demonstration of PKR

To a solution of benzyl ether (3a) of (S)-DMAP-alcohol (2) (75.1 mg, 0.252 mmol, (R), 95.8% ee) in $CH_2Cl_2$ (1.5 mL) at 0° C. was added (−)-menthyl chloroformate (0.051 mL, 0.238 mmol). In a second dry flask, a solution of 2,2,2,-trichloro-1,1-dimethyl chloroformate (0.26 M, 0.92 mL, 0.239 mmol) in $CH_2Cl_2$ was added to a solution of (3) of (R)-DMAP-alcohol (2) (56.3 mg, 0.253 mmol, 98.4% ee) in $CH_2Cl_3$ (1.5 mL) at 0° C. Both the reaction mixtures were warmed to room temperature and stirred for 2 hr. They were then added to a suspension of $MgBr_2$ (86.9 mg, 0.483 mmol, prepared by Grignard reaction of 1,2-dibromoethane with excess magnesium in THF in 0.5 mL diethyl ether. A clear colorless solution was obtained. After 10 min, the racemic 1-(1-naphthyl)ethanol (77.5 mg, 0.45 mmol) and triethylamine (0.0995 mL, 0.714 mmol) were added sequentially. The resulting clear solution was stirred at room temperature under a nitrogen atmosphere for 24 hr. The products and the alcohol substrate were isolated by running the reaction mixture through a silica gel plug (4–1.5 cm) eluted with 50:60 EtOAc/hexane (45 mL). The percent conversion of the alcohol was determined by $^1$H-NMR integration data. The product carbonate and the recovered alcohol were purified by flash column chromatography with 4:96 and 20:80 EtOAc/hexane as eluent, respectively. The enantiomeric and diastereomeric excess of these materials were determined by HPLC analysis on columns with chiral stationary phases. The product (9) was found to be a 91=9 ratio of enantiomers (82% ee). The product (10) is a mixture of diastereomers because the menthyl group constitutes a second chiral element, so the de value measures the extent of PKR with (10). The value of de is 70–75%. The error range (40–60% de) is due to partial overlap of signals used for assay.

It is understood that the general procedure for PKR, exemplified in Example 9 for specific reagents, is applicable to the chiral reagents being chemical compounds as illustrated and to their being biological catalysts, i.e., enzymes, as well. It is also contemplated that PKR is suitably utilized for a system in which both reagents are enzymes and for a mixed system which includes a chemical chiral reagent and an enzyme. For example, as to the latter, PKR of an acylation reaction may suitably include a chiral DMAP derivative and a lipase, the DMAP derivative reacting preferentially with one enantiomer and the lipase with the other enantiomer to form different predominant products which are separable.

In summary, the present invention provides novel catalytic reagents that are a combination of a chiral DMAP derivative, a chloroformate, a trialkylamine and a Lewis acid which react with a racemic mixture and resolve the enantiomers via kinetic resolution. The kinetic resolution technique is further improved by parallel kinetic resolution wherein resolved and separate chiral DMAP derivatives are the starting materials and each separately is reacted with a chloroformate to form separate and different pyridinium salts which are combined together with the Lewis acid to complete the reagent. The reagent is then reacted with the racemic alcohol to produce different, recoverable products, and different, recoverable DMAP derivatives if substituents such as $R^5$ in general formula (II) are varied.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation that lawfully can be accorded the appended claims.

We claim:

1. A chiral DMAP derivative which is represented by the general formula (II)

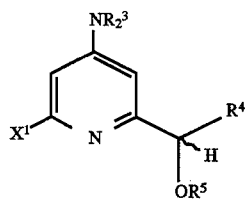

wherein $R^2$ is a $C_1$ to $C_7$ alkyl group or $NR^3{}_2$ is a cyclic amine group which is pyrrolidinyl, piperidinyl, piperazinyl or morpholinyl; $X^1$ is hydrogen, halogen, alkyl, aryl or heteroaryl; $R^4$ is a $C_1$ to $C_7$ branched or unbranched alkyl group; and $R^5$ is hydrogen, alkyl, benzyl, aryl, heteroaryl or acyl.

2. The DMAP derivative of claim 1, wherein $R^5$ is hydrogen.

3. A method of resolving a racemic mixture of a pair of enantiomers via kinetic resolution, comprising the steps of treating the racemic mixture with a reagent comprising a chloroformate; a trialkylamine, a Lewis acid and a chiral DMAP derivative having the general formula (II)

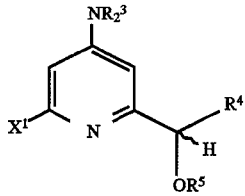

wherein $R^3$ is a $C_1$ to $C_7$ alkyl group or $NR^3{}_2$ is a cyclic amine group which is pyrrolidinyl, piperidinyl, piperazinyl or morpholinyl; $X^1$ is hydrogen, halogen, alkyl, aryl or heteroaryl; $R^4$ is a $C_1$ to $C_7$ branched or unbranched alkyl group; and $R^5$ is hydrogen, alkyl, benzyl, aryl, heteroaryl or acyl, to form a product of one of the enantiomers and separating the product.

4. The method of claim 3, wherein said Lewis acid has the formula $MX_n$ wherein M is a cation selected from the group consisting of cations of the elements of Group IIA, Group IIIa and Group VIII; wherein X is an anion selected from the group consisting of onions of elements of Group VIIA; and n is an integer having a value of 2 or 3.

5. The method of claim 3, wherein said chloroformate has the formula (I):

$$Cl-C(O)-OR^2 \quad (I)$$

wherein $R^2$ is menthyl, cyclohexyl, ethyl, 1-adamantyl, 9-fluorenyl-methyl. trichloroethyl, phenyl or vinyl.

6. The method of claim 5, wherein the compound of formula (I) is $Cl_3C-C(CH_3)_2-O-C(O)-Cl$.

7. The method of claim 3, wherein the racemic mixture is a secondary alcohol, a secondary amine or an alkene.

8. The method of claim 7 wherein said racemic mixture is a secondary alcohol which has the formula $R^1CH(CH_3)OH$ wherein $R^1$ is an aryl or alkenyl group.

9. A composition comprising in admixture, which is capable of resolving a racemic mixture, a chloroformate, a trialkylamine, a Lewis acid and a chiral DMAP derivative having the general formula (II)

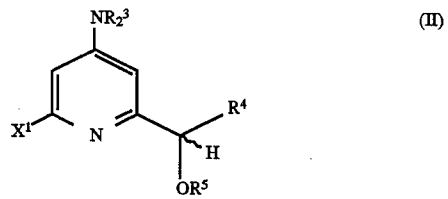

wherein $R^3$ is a $C_1$ to $C_7$ alkyl group or $NR^3{}_2$ is a cyclic amine group which is pyrrolidinyl, piperidinyl, piperazinyl or morpholinyl; $X^1$ is hydrogen, halogen, alkyl, aryl or heteroaryl; $R^4$ is a $C_1$ to $C_7$ branched or unbranched alkyl group; and $R_s$ is hydrogen, alkyl, benzyl, aryl, heteroaryl or acyl.

10. The composition of claim 9 wherein said Lewis acid is a compound of a cation selected from the group consisting of $Zn^{2+}$, $Mg^{2+}$, $Ca^{2+,\ Ni2+}$, and $Fe^{3+}$ and an onion selected from the group consisting of $Cl^-$, $Br^-$, $OSO_2CF^{-1}{}_3$, $NO^{-1}{}_3$ and $BF^-{}_4$.

11. The composition of claim 10 wherein said Lewis acid is $ZnCl_2$ or $MgBr_2$.

12. The composition of claim 9 wherein said chloroformate has the formula (I):

$$Cl-C(O)-OR^2 +tm \quad (I)$$

wherein $R^2$ is a group which is a menthyl, a cyclohexyl, a 1-adamantyl, a 9-fluorenyl-methyl, a trichloroethyl, a phenyl or a vinyl.

13. The composition of claim 12, wherein the compound of formula (I) is $Cl_3C-C(CH_3)_2-O-C(O)-Cl$.

14. The composition of claim 9, wherein said chloroformate is substituted with a compound of the general formula Cl-Y where Y is a functional group which is

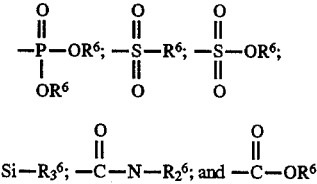

wherein $R^6$ is hydrogen, alkyl, benzyl, aryl, heteroaryl or acyl.

15. A method of resolving a racemic mixture of a pair of enantiomers, comprising the steps of treating the mixture with a reagent comprising a trialkylamine, a Lewis acid, a first DMAP derivative formed from a first chiral DMAP compound and a first chloroformate, a second DMAP derivative formed from a second chiral DMAP compound of opposite chirality and a second chloroformate, to form a different predominant product for each of said enantiomer pair and separating the products, said first and second DMAP compounds having the general formula (II)

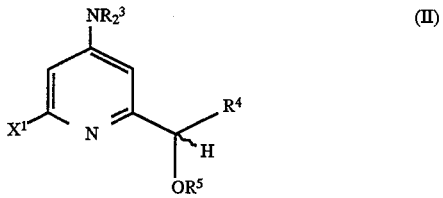

wherein $R^3$ is a $C_1$ to $C_7$ alkyl group or $NR^3{}_2$ is a cyclic amine group which is pyrrolidinyl, piperidinyl, piperazinyl or morpholinyl; $X^1$ is hydrogen, halogen, alkyl, aryl or heteroaryl; $R^4$ is a $C_1$ to $C_7$ branched or unbranched alkyl group; and $R^5$ is hydrogen, alkyl, benzyl, aryl, heteroaryl or acyl, and wherein $R^4$, $R^3$, $R^5$ or $X^1$ for said first compound is different from $R^4$, $R^3$, $R^5$ or $X^1$ for said second compound.

16. The method of claim 15 wherein said first DMAP compound is represented by the formula

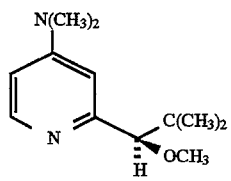

and said second DMAP compound is represented by the formula

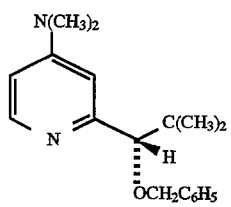

17. A composition comprising in admixture, which is capable of resolving a racemic mixture, a trialkylamine, a Lewis acid, a first DMAP derivative formed of a first chiral DMAP compound and a first chloroformate, a second DMAP derivative formed of a second DMAP derivative of opposite chirality and a second chloroformate, said first and second DMAP compounds having the general formula (II)

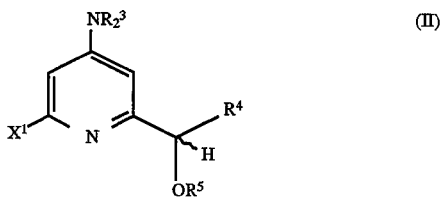

wherein $R^3$ is a $C_1$ to $C_7$ alkyl group or $NR^3{}_2$ is a cyclic amine group which is pyrrolidinyl, piperidinyl, piperazinyl or morpholinyl; $X^1$ is hydrogen, halogen, alkyl, aryl or heteroaryl; $R^4$ is a $C_1$ to $C_7$ branched or unbranched alkyl group; and $R^6$ is hydrogen, alkyl, benzyl, aryl, heteroaryl or acyl, and wherein said first derivative is of opposite chirality from said second derivative.

18. The composition of claim 17 wherein said first DMAP compound is represented by the formula

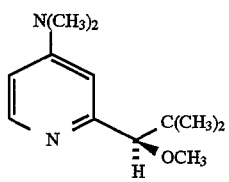

and said second DMAP compound is represented by the formula

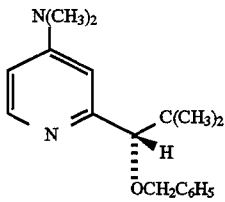

19. A composition comprising in admixture, which is capable of resolving a racemic mixture of a pair of enantiomers, a first chiral reagent reactive to one of said pair of enantiomers, a second chiral reagent of opposite chirality to said first reagent reactive with the other one of said pair, in a single phase solvent sufficient to support reaction of said first reagent with one of said pair of enantiomer and said second reagent with the other of said pair of enantiomers, wherein said first and second reagents are DMAP derivatives having the general formula (II)

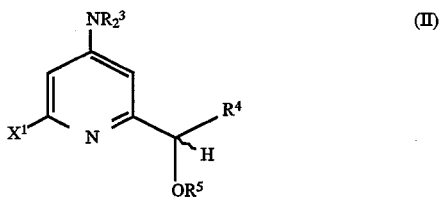

wherein $R^3$ is a $C_1$ to $C_7$ alkyl group or $NR^3{}_2$ is a cyclic amine group which is pyrrolidinyl, piperidinyl, piperazinyl or morpholinyl; $X^1$ is hydrogen, halogen, alkyl, aryl or heteroaryl; $R^4$ is a $C_1$ to $C_7$ branched or unbranched alkyl group; and $R^s$ is hydrogen, alkyl, benzyl, aryl, heteroaryl or acyl, and wherein said first derivative is of opposite chirality from said second derivative.

20. The composition of claim 19, wherein said solvent comprises a trialkylamine and a Lewis acid.

21. A method of resolving a racemic mixture of a pair of enantiomers, comprising the steps of treating the mixture with a reagent comprising a first chiral reagent reactive with one of said pair, a second chiral reagent of opposite chirality reactive with the other one of said pair, in a single phase solvent sufficient to support reaction of said first reagent with one of said pair of enantiomer and said second reagent with the other of said pair of enantiomers to form a different predominant product for each of said enantiomer pair and separating the products, wherein said first and second reagents are chiral DMAP derivatives having the general formula (II)

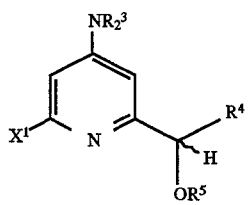 (II)

wherein $R^3$ is a $C_1$ to $C_7$ alkyl group or $NR^3_2$ is a cyclic amine group which is pyrrolidinyl, piperidinyl, piperazinyl or morpholinyl; $X^1$ is hydrogen, halogen, alkyl, aryl or heteroaryl; $R^4$ is a $C_1$ to $C_7$ branched or unbranched alky group; and $R^6$ is hydrogen, alkyl, benzyl, aryl, heteroaryl or acyl, and wherein said first derivative is of opposite chirality from said second derivative.

22. The method of claim 21, wherein said solvent includes a trialkylamine and s Lewis acid.

* * * * *